United States Patent [19]

Cosman

[11] Patent Number: 4,808,611

[45] Date of Patent: Feb. 28, 1989

[54] USE OF INTERLEUKIN-1 TO INDUCE DEVELOPMENT OF MULTIPOTENT HEMOPOIETIC CELL POPULATIONS

[75] Inventor: David J. Cosman, Seattle, Wash.

[73] Assignee: Immunex Corporation, Seattle, Wash.

[21] Appl. No.: 891,929

[22] Filed: Jul. 30, 1986

[51] Int. Cl.[4] .............................................. A61K 37/00
[52] U.S. Cl. ........................................ 514/12; 530/351
[58] Field of Search ...................... 435/240.002; 514/8, 514/12; 530/351

[56] References Cited

PUBLICATIONS

BA 83(9): 82719, 1987.
BA 81(9): 80944, 1986.
CA 104(25): 104: 223263e, 1986.
CA 106(5): 31170s, 1987.
CA 106(17): 136887h, 1987.
Schrader et al., "Structural Homologies Among the Hemopoietins," *Proc. Natl. Acad. Sci. U.S.A.*, 83:2458 (1986).
Clark and Kamen, "The Human Hematopoietic Colony-Stimulating Factors," *Science*, 236:1229 (1987).
Mochizuki et al., "Interleukin 1 Regulates Hematopoietic Activity, a Role Previously Ascribed to Hemopoietin 1," *Proc. Natl. Acad. Sci. U.S.A.* 84: 5267 (1987).
Moore and Warren, "Synergy of Interleukin 1 and Granulocyte Colony-Stimulating Factor: In Vivo Stimulation of Stem-Cell Recovery and Hematopoietic Regeneration Following 5-Fluorouracil Treatment of Mice," *Proc. Natl. Acad. Sci. U.S.A.* 84:7134 (1987).
Bartelmez and Stanley, "Synergism Between Hemopoietic Growth Factors (HGFs) Detected by Their Effects on Cells Bearing Receptors for a Lineage Specific HGF: Assay of Hemopoietin-1", *J. Cell. Physiol.* 122:370 (1985).
Jubinsky and Stanley, "Purification of Hemopoietin 1: A Multilineage Hemopoietic Growth Factor", *Proc. Natl. Acad. Sci. U.S.A.* 82:2764 (1985).
Stanley et al., "Regulation of Very Primitive, Multipotent, Hemopoietic Cells by Hemopoietin-1", *Cell* 45:667 (1986).
Oppenheim et al., "There Is More Than One Interleukin 1", *Immunol. Today* 7:45 (1986).
Durum et al., "Interleukin 1: An Immunological Perspective", *Ann. Rev. Immunol.* 3:263 (1985).

*Primary Examiner*—John W. Rollins
*Attorney, Agent, or Firm*—Scott G. Hallquist

[57] ABSTRACT

Interleukin-1, in conjunction with one or a mixture of selected colony-stimulating factors, is capable of inducing the development of primitive multipotent hemopoietic cell populations.

10 Claims, No Drawings

USE OF INTERLEUKIN-1 TO INDUCE DEVELOPMENT OF MULTIPOTENT HEMOPOIETIC CELL POPULATIONS

BACKGROUND OF THE INVENTION

The present invention relates generally to lymphokines, and specifically to use of particular lymphokines to promote differentiation and proliferation of hematopoietic stem cells.

Hemopoiesis refers to a process by which various mature blood cell types develop from developmentally multipotent stem cells found in hemopoietic, or blood-cell forming, tissues. These tissues are found in various body locations for example, bone marrow, spleen and thymus. In this process, distinct subpopulations of progenitor cells arise from more primitive, undifferentiated stem cells. Subsequent developmental events result in differentiation of mature classes of blood cells (for example, granulocytes, monocytes, eosinophils, megakaryocytes, and mast cells) from progenitor cell subpopulations.

Recent investigations of hemopoiesis have begun to elucidate the role of various hormone-like proteins or growth factors as effectors of hemopoiesis. Growth factors regulating early stages in the differentiation pathway are known collectively as multilineage growth factors. Those involved in later stages, wherein specialized cell types develop from precursor cells, are knwon as lineage-specific growth factors. Synergism between lineage-specific and multilineage growth factors appears to play a regulatory role in the ontogeny of blood cells.

Exemplary of such synergistic relationships are the joint activities of the growth factor heretofore designated hemopoietin-1 (H-1), and certain lineage-specific colony stimulating factors. H-1 is a multilinear growth factor identified by its capacity to induce development of multipotent stem cells in concert with other growth factors. In the absence of GM-CSF or other colony stimulating factor, H-1 exhibits no detectable effects in cultures of developmentally primitive hemopoietic cells. However, in the presence of GM-CSF, CSF-1, or certain other colony stimulating factors, H-1 stimulates cell growth and differentiation of hemopoietic cells more primitive than those capable of being induced by any of the colony stimulating factors alone. Preliminary characterization studies of hemopoietin-1 isolated from serum-free cultures of human bladder carcinoma cells and assayed in concert with CSF-1 a monocyte/macrophage lineage-specific growth factor, have been reported by Bartelmez et al., *J. Cell. Phys.* 122:370 (1985), Jubinski et al., *Proc. Natl. Acad. Sci. USA* 82:2764 (1985), and Stanley et al., *Cell* 45:667 (1986).

In view of the capacity of hemopoietin-1 to induce cell development at the earliest stages of hemopoiesis, considerable interest has developed in this growth factor as a therapeutic agent. Therapeutic utilities for a protein having the activity attributed to hemopoietin-1 include treatment of hematological anamalies resulting from chemotherapy, radiation treatment or exposure, enhancement of immune responses to viral or bacterial pathogens; treatment of leukemia; and use in conjunction with bone marrow transplants.

Interleukin-1 (IL-1) activity is attributable to proteins released by macrophages and other cell types in response to immunogenic stimulation. This family of proteins has been associated with a complex spectrum of biological activities. IL-1 is a primary immunostimulatory signal capable of inducing thymocyte proliferation via induction of interleukin-2 release, and stimulating proliferation and maturation of B-lymphocytes. In addition, IL-1 has been linked with prostaglandin production and induction of fever, and with promotion of wound healing. Useful reviews of the literature relating to IL-1 include Oppenheim at al., *Immunol. Today* 7:45 (1986), and Durum et al., *Ann. Rev. Immunol.* 3:263 (1985).

Prior to the present invention, IL-1 had not been observed to exhibit activity as a multilineage hemopoietic growth factor. The present invention resides in the unexpected discovery that the biological activity of IL-1, in concert with GM-CSF, is coincident with that of the growth factor heretofore termed hemopoietin-1. Further, physicochemical and serological criteria indicate that IL-1 and hemopoietin-1 are identical. This discovery was facilitated by recent inventions which enabled production of useful quantities of substantially homogeneous recombinant human IL-1.

SUMMARY OF THE INVENTION

The present invention provides a method of inducing proliferation and differentiation of hemopoietic stem cells in a mammal, comprising administering to the mannual an effective quantity of interleukin-1 in conjunction with an effective quantity of a colony stimulating factor. In its most preferred aspects, the present invention provides methods of treating humans to induce hemopoietic cell development.

DETAILS OF THE INVENTION

IL-1 activity resides in two distantly related proteins, herein disignated IL-1α and IL-1β (March et al., *Nature* 315:641 (1985)). Both molecules are normally synthesized as larger precursors having molecular weights of about 30,000 daltons; which are subsequently proteolytically processed to yield mature forms having molecular weights of approximately 17,500 daltons. However, unlike IL-1α, the larger precursor of IL-1β is not biologically active prior to proteolytic cleavage to its mature form. All active forms of IL-1α and IL-1β are useful in the treatment methods of the present invention. As used herein, "interleukin-1" and "IL-1" refer collectively to natural and recombinant forms of both IL-1α and IL-1β. In addition, the term comprehends proteins having amino acid sequences substantially identical to that of native mammalian forms of IL-1α and IL-1β, which possess biological activity relative to hemopoiesis which is common with that of native forms. Substantial identity of amino acid sequences means that the sequences are identical or differ by one or more amino acid alterations (deletions, additions, or substitutions) that do not cause an adverse functional dissimilarity between the synthetic protein and the native form.

As used throughout the specification in a generic or collective sense, "colony stimulating factor" refers to a family of lymphokines which induce progenitor cells found in bone marrow to differentiate into mature blood cell types. Specific colony stimulating factors, or CSFs, which are included within the foregoing class include the following:

(1) granulocyte-macrophage colony stimulating factor (GM-CSF); Cantrell et al., *Proc. Nat. Acad. Sci. USA* 82:6250 (1985);

(2) granulocyte colony stimulating factor (G-CSF); Nicola et al., *J. Biol. Chem.* 258:9017 (1983); Souza et al., *Science* 232:61 (1986);

(3) macrophage colony stimulating factor (M-CSF or CSF-1); Kawasaki et al., *Science* 230:291 (1985); Stanley et al., *J. Cell. Biochem.* 21:151 (1983);

(4) erythropoietin (Epo); Miyake et al., *J. Biol. Chem.* 252:5558 (1977)); and (5) erythroid-potentiating activity (EPA; also known as BPA, or burst-promoting activity); Westbrook et al., *J. Biol. Chem.* 259:9992 (1984); Gasson et al., *Nature* 315:768 (1985).

Individual CSFs can be purified from media conditioned by particular cell lines, or in some cases, expressed by recombinant organisms or cells. GM-CSF can be cloned and expressed by the methods disclosed in U.S. patent applications Ser. Nos. 750,401, filed 07/02/85 and 763,130 filed 08/06/85. The disclosures of these applications, and the foregoing cited articles, are incorporated by reference herein.

IL-1β can be purified from cell cultures of peripheral blood leukocytes, essentially as described in commonly-assigned copending U.S. patent applications Ser. Nos. 622,201, filed 06/19/84, 635,006, filed 07/27/84, and 676,533 filed 11/30/84. However, recent experiments have indicated that recombinant forms of IL-1α and IL-1β (rIL-1α and rIL-1β) can be efficiently produced using bacterial expression systems. Thus, these forms are preferred. Details of production by these techniques are provided in the following paragraphs.

1. Production of rIL-1α and rIL-1β

A. Construction of bacterial expression vectors

Mature IL-1α and IL-1β can be expressed in *E. coli* under the control of the phage λ PL promoter and cI857ts thermolabile repressor. Expression plasmids for rIL-1α and rIL-1β production can be constructed from plasmid pPLc28 (ATCC 53082), plasmid pKK223-3 (available commercially from Pharmacia Fine Chemicals, Uppsala, Sweden) and plasmids containing IL-1α cone 10A (March et al., supra; ATCC 39997) and IL-1β cone IL-1-14 (ATCC 39925) as follows.

To create an expression vector of IL-1α, a 3' portion of the IL-1α gene, extending from $Ser^{113}$ (nucleotides 337-339) to $Ala^{271}$ (nucleotides 811-813) is inserted into expression vector pPLc28. This is achieved by excising a 499 base pair AluI-NdeI fragment from the 10A clone, to which the following synthetic oligonucleotide linker is joined:

```
AATTCTAGGATAATTA  ATG  TCA  GCA  CCT  TTT  AG
    GATCCTATTAAT  TAC  AGT  CGT  GGA  AAA  TC
```

This linker includes AluI and EcoRI termini, a ribosome binding site, and ATG initiation codon in addition to the IL-1α $Ser^{113}$-$Ser^{117}$ sequence. pPLc28 is then digested to completion with EcoRI and NdeI, and the resulting larger fragment isolated by agarose gel electrophoresis. The linker, 10A clone, and plasmid fragments are then fused using T4 ligase, to provide an expression plasmid herein denoted pILPα. Additional details of the construction of pILPα can be found in the disclosure of the copending, commonly assigned U.S. patent application Ser. No. 721,765, filed 04/10/85, the disclosure of which is incorporated by reference herein.

The resulting construct is then employed to transform *E. coli* strain ΔH1 (ATCC 33767; Castellazi et al., *Molec. gen. Genet.* 117:211) to ampicillin resistance, using standard techniques. To express the plasmid-borne IL-1α gene, cultures of transformed ΔH1 are grown in L-broth without ampicillin. When the cultures reach an $A_{729}$ of about 0.5 the culture temperature is raised to about 43° C. to promote derepression of the thermolabile PL promoter. After one hour at elevated temperature, cells are harvested by centrifugation and flash-frozen in a dry-ice/methanol mixture. IL-1α activity in cell extracts can be assayed by either the thymocyte mitogenesis or IL-1 conversion assays disclosed by Conlon, *J. Immun.* 131:1280 (1983), Kronheim et al., *J. Exp. Med.* 161:490 (1985) and also in copending U.S. patent application Ser. No. 721,765, the disclosure of which is incorporated by reference herein. Details regarding purification procedures are provided below.

rIL-1β can be produced via construction of an analogous plasmid, herein designated pILPβ. This vector is assembled from pILPc (March et al., supra), which is constructed by replacing the BamHI/EcoRI fragment of pKK223-3 with a Sau3A/EcoRI fragment from pPLc28 containing the λ PL promoter. This plasmid is digested to completion with EcoRI and PstI, and the largest fragment then ligated to a (1) a 669 base pair HpaII/PstI fragment from pIL-1-14 (ATCC 39925) containing the human IL-1β gene ($ALa^{117}$ to COOH terminus encodes active protein) and (2) the following EcoRI/HpaI synthetic oligonucleotide:

```
AATTCTAGGATAATTA  ATG  GCA  CCT  GTA  CGA  TCA  CTG  AAC  TGC  ACG  CTC
    GATCCTATTAAT  TAC  CGT  GGA  CAT  GCT  AGT  GAC  TTG  ACG  TGC  GAF  GC
```

Plasmid pILPβ is then used to transform *E. coli*, H1 or other cells containing a thermolabile repressor of PL transcription. Following growth to $A_{729}$ of about 0.5, expression of the rIL-1β gene is obtained by heat induction as previously described. rIL-1β activity, as in the case of rIL-1α, can be identified using the thymocyte mitogenesis or IL-1 conversion assays cited above.

B. Protein Purification

The general purification scheme employed to provide homogeneous protein involves an initial acid extraction from cell pellets, followed by an SPS (Sulphopropyl Sephadex; Pharmacia) column chromatography step and elution from a DEAE-Sephacel (Pharmacia) column. Column fractions containing rIL-1α are then applied to Phenyl Sepharose CL-4B (Pharmacia), while those containing rIL-1β are applied to a Procion Red agarose (Bethesda Research Laboratories, Gaithersburg, Md., USA) column for final purification. Sterile buffers are used throughout the purification protocol to safeguard product from contamination by endotoxin. Chromatography fractions can be monitored for protein concentration by the Bio-rad total protein assay (Bio-rad Laboratories, Richmond, Calif., USA) and the progress of purification evaluated by SDS-PAGE as described by Kronheim, *J. Exp. Med.* 161:490 (1985) or other suitable technique. IL-1 activity of column fractions can be determined by the IL-1 assays previously referenced.

Experiments in which the pH of the initial extraction buffer was varied indicate that extraction of rIL-1α from *E. coli* cell suspensions at pH 2.8 results in precipitation of significant quantities of contaminating proteins while enabling good recovery of rIL-1α. However, buffers having pH(s) varying between 2.0 and 3.5 can be employed with success. Similar experiments involving rIL-1β have shown that pH 3.9 is optimal for precipitating unwanted proteins while solubilizing rIL-1β. However, extraction buffers having pH varying between 3.5 and 4.5 can be successfully employed. The optimal pH for this initial extraction step may vary between fermenter batches. For this reason, small-scale pilot runs may be employed to determine optimal pH, particularly where large quantities of material are involved.

To achieve the initial acid extraction, cell pellets obtained as described above are suspended in 30 mM Tris-HCl buffer, pH 8, containing 5 mM EDTA and 1 mM phenylmethylsulfonyl fluoride (PMSF), such that about 20 ml buffer is employed to suspend the pellet obtained from about 2.5 liters *E. coli* culture. The resulting suspension is rapidly frozen in a dry ice/methanol bath and then thawed. Next, 200 ml of 30 mM sodium citrate buffer at the selected pH, containing 5 mM EDTA and 250 μg/ml lysozyme is added to the suspensions. The resulting acid suspensions are incubated for 60 minutes in a 37° C. water bath. Following incubation, the extracts are rapidly frozen in a dry-ice/methanol bath, thawed, and then centrifuged at 4° C. for 45 minutes at 38,000×g. Supernatants are then carefully decanted for use in the next purification step.

Supernatants from the foregoing extraction step are applied to an SPS C-25 column which has been preconditioned with 0.1% Triton X-100 (polyoxyethylene ether; Sigma Chemical Company, St. Louis, Mo. USA) and 10% fetal calf serum to reduce nonspecific absorption of IL-1 activity to the resin. First, the pH of the crude extracts is raised to about 4.0 by addition of 1.0 N NaOH, and then the resulting solutions are applied to 20×2.5 cm columns containing SPS C-25 previously equilibrated with 10 mM sodium citrate, pH 4.0. The columns are washed with 3 column volumes 10 mM 2-(N-morpholino)ethanesulfonic acid (MES) buffer, pH 5.0, and desired protein is eluted from the column with 10 mM Tris-HCl, pH 8.1. 10 ml fractions are collected, analyzed by SDS-PAGE, and stored at 4° C. for additional purification.

Fractions containing IL-1 activity from the previous step are combined and then applied to 15×2.5 cm columns containing DEAE-Sephacel previously equilibrated with 10 mM Tris-HCl pH 8.1. The DEAE columns are washed with five column volumes of the starting buffer and then eluted with linear gradients of NaCl in a total of two column volumes. To elute rIL-1α, a gradient ranging from 0-600 mM NaCl is employed; for rIL-1β, a gradient from 0-400 mM NaCl is used (both gradients in 10 mM Tris-HCl pH 8.1) 5 ml fractions are collected, analyzed by SDS-PAGE, and held at 4° C. for further purification.

Fractions containing rIL-1α are treated by addition of sufficient solid ammonium sulfate to provide a final concentration of 0.5 M. The resulting solution is then applied to a 30×2.5 cm column containing Phenyl Sepharose CL-4B, equilibrated with 10 mM Tris-HCl buffer, also 0.5 M in ammonium sulfate, at pH 8.1. The column is washed with 5 column volumes starting buffer, and eluted with a decreasing linear gradient of ammonium sulfate, starting at 0.5 M and ending at 0 M in about 3 column volumes. Finally, the column is eluted with about 100 ml 10 mM Tris-HCl, pH 8.1. 10 ml fractions are collected, and those containing rIL-1α are pooled and concentrated by reapplication to SPS C-25 as described by Kronheim et al., supra. rIL-1α is eluted using 10 mM phosphate buffered saline (PBS) at pH 8.2.

Fractions containing rIL-1β resulting from the DEAE column step are diluted 1:4 in 10 mM Tris-HCl buffer, pH 8.1, to reduce ionic strength to less than 40 mM, then applied to a 20×2.5 cm column containing Procion Red agarose previously equilibrated with 10 mM Tris-HCl buffer, pH 8.1. The column is washed with five column volumes of starting buffer, and then eluted with a linear gradient in five column volumes ranging from 0 to 1 M NaCl in 10 mM Tris-HCl buffer, pH 8.1. Fractions of 10 ml are collected, analyzed, and then concentrated as described for rIL-1α, above.

Purified rIL-1α and rIL-1β are stored at −70° C.

C. Assay of Hemopoietic Cell Induction

To assay hemopoietic growth factor activity, samples are evaluated for their capacity, in conjunction with a particular CSF, to induce proliferation of murine nonadherent bone marrow cells following administration of 5-fluorouracil. Although GM-CSF is employed in the assay described below, other colony stimulating factors could be employed to detect hermopoietic cell inductive activity.

8–12 week old C3H/Hej mice (The Jackson Laboratory) are administered 5-fluorouracil at a dosage of 150 mg/kg IV. The day following this treatment, the animals are sacrificed and femurs and tibias removed. Muscle tissue is removed and the bones are held at 4° C. in media. The media employed throughout the assay procedure is RPMI 1640, supplemented with 10% horse serum (HS), containing 25–50 μg/ml penicillin, streptomycin, and gentamycin and $5 \times 10^{-5}$ M 2-mercaptoethanol. Initial collection of bone marrow cells is done in media without serum, however.

A syringe is filled with cold media, and the joint caps or ends of the bones are snipped with scissors. Marrow cells are expressed from the bones by injection of media through 25 gauge needle. 4 ml media are used for each femur, while 2 ml are used per tibia. The cell clumps are then broken up by passage through an 18 gauge needle 3 times. Next, the cells are passed once through a 22 gauge needle, and then finally expressed through a 25 gauge needle into a polypropylene tube. The resulting suspension is then centrifuged at 1000–2000 rpm at 6°–10° C. The cells are then harvested and resuspended in fresh media with serum to provide a concentration of $6 \times 10^5$ viable nucleated cells per ml.

Cells are plated in a 96 well flat bottom microtiter plate, in a volume of 50 μl, against a dilution series of the samples to be assayed. Each sample contains, in a volume of 50 μl, sample diluted with media containing 20 units/ml GM-CSF, which has been HPLC purified as described by Cantrell et al., *Proc. Nat. Acad. Sci. USA* 82:6250 (1985) and also in copending U.S. patent application Ser. No. 750,401, the disclosure of which is hereby incorporated by reference. As a negative control, wells are prepared containing only GM-CSF.

As a positive control, samples of concentrated supernatants of cultured HBT 5637 adherent human bladder carcinoma cells (ATCC HTB9), serially diluted in 20 units/ml GM-CSF, are employed. To obtain medium containing H-1 activity, cells are grown to confluence in RPMI-1640 medium supplemented with 10% fetal calf serum (FCS). After the cells reach confluence, media is decanted and replaced with fresh RPMI-1640 containing 0.1% FCS. The cells are then cultured for 72 hours in humidified atmosphere of 5% $CO_2$ in air. The resulting conditioned medium is then harvested and centrifuged at $2000 \times g$ to remove cellular debris and used immediately or frozen for future use. Medium can be concentrated by precipitating proteins with ammonium sulfate (80% saturation), then resuspending and dialyzing in PBS, pH 7.2, at 4° C.

The plates containing the samples to be assayed are incubated at 37° C. in 5% $CO_2$ for 72 hours. At the conclusion of this period cells are pulsed by addition of 2 $\mu$Ci $^3$H-thymidine (Du Pont, Wilmington, Del., USA; 70–80 Ci/mM) in 25 $\mu$l for 16–18 hours. Cells are harvested on glass fiber filters, lysed with distilled, deionized water, and analyzed for incorporated radioactivity by liquid scintillation counting. Units of H-1 activity are calculated relative to the positive control standards. Units of activity are defined as the reciprocal of the dilution required to give 50% maximum cpm relative to the standard.

D. Administration of IL-1

In practicing the method of the present invention, purified IL-1 is administered to a mammal in need of treatment at a therapeutically effective dosage level. Effective dosage levels are determined by initiating treatment at lower dosage levels and elevating the amounts of IL-1 administered until hemopoietic cell proliferation and differentiation are achieved. Generally, therapeutic dosages will range from 10 to 1,000,000 units H-1 activity per kg body weight, in conjunction with 10 to 1,000,000 units per kg colony-stimulating factor activity. The colony stimulating factor employed can be GM-CSF, G-CSF, CSF-1, Epo, or EPA, or a mixture of colony stimulating factors, depending upon the therapeutic result intended.

Injection offers the most practical method of administration, either intravenously, intramuscularly, or intraperitoneally. Neutral buffered saline or saline mixed with conspecific serum albumin are appropriate diluents. Preferably, conspecific forms of IL-1 are employed.

The following example describes serological and physicochemical studies indicating that IL-1 and the factor previously known as hemopoietin-1 are identical.

EXAMPLE

1. Copurification of H-1 and IL-1 Activity from HBT CM

Conditioned medium (CM) harvested from HBT cell cultures was concentrated using a hollow fiber ultrafiltration device having a 10,000 Dalton molecular weight cutoff. The resulting concentrated CM was adjusted to 20 mM Tris-HCl, pH 7.5, and 0.01% Tween 20 (polyoxyethylenesorbitan monolaurate, Sigma) and contacted with a slurry of Sepharose CL-6B-200 in the same buffer at 4° C. Solid ammonium sulfate was then slowly added to the slurry, with stirring, to provide a final concentration of about 75% saturation. The resulting mixture was allowed to equilibrate overnight, and then the resin was recovered to vacuum filtration, and poured into a column. The column was eluted with a gradient fom 3 M to 0 M ammonium sulfate in 20 mM Tris-HCl, pH 7.5, 0.2% Tween 20. Fractions were collected dialysed against an appropriate buffer, and assayed to H-1 activity by the 5-fluorouracil bone marrow assay described above. Active fractions (about 136 ml) were pooled and applied to a $1.6 \times 11$ cm (22 ml) column containing Phenyl Sepharose CL-4B, which had been previously equilibrated with 1M $(NH_4)_2SO_4$, 20 mM Tris-HCl, pH 7.5, 0.02% Tween 20. The column was then washed with one volume of the equilibration buffer, and then eluted with a gradient ranging from 1 M to 0 M $(NH_4)_2SO_4$. 10 ml fractions were collected, dialyzed against appropriate buffers, and then assayed in both the 5-fluorouracil bone marrow assay and the IL-1 conversion assays. Peak activities in each assay were observed in coinciding fractions.

2. Comparison of H-1 Activity Purified from HBT-CM and Purified Recombinant IL-1α and IL-1β in a 5-Fluorouracil Bone Marrow Assay and IL-1 Conversion Assays Fractions containing H-1 activity from the purification procedure described above, as well as an immune precipitate of H-1 activity from HBT-CM, were assayed in the IL-1 conversion assay and 5-fluorouracil H-1 assays. Samples of purified recombinant IL-1α and IL-1β (10 μg/ml) were similarly assayed. The results appear in Table 1, below:

TABLE 1

| Assay Comparison of Activities of H-1 from HBT-CM and Recombinant IL-1α and IL-1β | | |
|---|---|---|
| Sample | IL-1 Activity (Units/ml) | H-1 Activity (Units/ml) |
| HBT Crude concentrate | 78,000 | 474 |
| Sepharose CL-6B (peak) | $18.4 \times 10^6$ | 1334 |
| Phenyl Sepharose (peak) | $14 \times 10^6$ | 700 |
| Immune precipitate | $4 \times 10^6$ | 326 |
| Recombinant IL-1α | $1 \times 10^9$ | 843,000 |
| Recombinant IL-1β | $1 \times 10^9$ | 47,000 |

3. Immunoprecipitation of H-1 Activity from HBT CM Phenyl Sepharose fractions with Rabbit Polyclonal anti-IL-1α and anti IL-1β

Anti-IL-1α and anti-IL-1β antisera were employed in precipitate H-1 activity purified from HBT CM as follows. 200 μl antisera (anti-IL-1α, anti-IL-1β, or a mixture) diluted 1:50 or 1:500 in 1640 media containing 1 mg/ml bovine serum albumin was added to 200 μl of purified H-1 in a 1.5 ml capped tube and the resulting solution incubated 30 minutes at 4° C. with gentle agitation. 200 μl Protein A agarose (20% in 1640 media; Bio-rad) were then added to each tube and the tubes incubated overnight at 4° C. Each tube was then centrifuged 3 minutes at 4° C., and supernatants were decanted and reserved for assay. The agarose pellet in each tube was then washed twice with 400 μl 1640 media containing 10% FCS, and then contacted with 400 μl 0.1M glycine-HCl pH 3.0. The resulting mixtures were incubated 30 minutes at 22° C. with gentle mixing and centrifuged. The supernatants, containing protein bound by the antisera, were collected and assayed by the 5-fluorouracil and IL-1 conversion assays. The results appear in Table 2, below.

TABLE 2

Immunoprecipitation and Recovery of H-1 and IL-1 Activity Using Anti-IL-1α and Anti-IL-1β Antisera

| | (H-1 Activity and IL-1 Activity in Units/ml) | | | |
|---|---|---|---|---|
| | Supernatants | | Glycine-HCl Extracts | |
| Antisera | H-1 | IL-1 | H-1 | IL-1 |
| None | 326 | 4 × 10$^6$ | — | — |
| prebleed serum | | | | |
| 1:50 | 326 | >4 × 10$^6$ | — | 610 |
| 1:500 | 166 | >4 × 10$^6$ | — | 435 |
| anti-IL-1α | | | | |
| 1:50 | — | 43 | — | 1.6 × 10$^6$ |
| 1:500 | 138 | 97,356 | 112 | 1.9 × 10$^6$ |
| anti-IL-1β | | | | |
| 1:50 | 136 | 155,037 | — | 706 |
| 1:500 | 90 | >4 × 10$^6$ | — | 285 |
| Both | | | | |
| 1:50 | — | 674 | 138 | 2.4 × 10$^6$ |
| 1:500 | 68 | 110,761 | 31 | 277,279 |

The results of this experiment indicate that anti-IL-1α precipitates H-1 and IL-1 activities purified from HBT-CM as measured by the IL-1 conversion and 5-fluorouracil bone marrow proliferation assays. The bound activity can be recovered in a glycine-HCl extract. No H-1 activity could be detected that was not precipitated by anti-IL-1α. Antisera to IL-1β also bound some H-1 activity.

A protein electrophoresis/immunoblotting experiment (Western blot) was conducted in which a protein sample containing H-1 activity from HBT-CM was size-separated by gel electrophoresis, transferred to a substrate, and exposed to anti-IL-1α. Protein bands on the substrate which wound antibody were then detected using peroxidase-conjugated anti-mouse IgG and an appropriate stain. This experiment indicated that the protein sample contained a component bound by anti-IL-1α and exhibiting a molecular weight indistinguishable from that of purified recombinant IL-1α.

What is claimed is:

1. A method of inducing proliferation and differentiation of hemopoietic stem cells in a mammal, comprising administering to the mammal an effective quantity of interleukin-1 (IL-1) in conjunction with an effective quantity of a colony stimulating factor.

2. A method according to claim 1, wherein the colony stimulating factor is selected from the group consisting of GM-CSF, CSF-1, G-CSF, erythropoietin, and EPA.

3. A method according to claim 2, wherein the IL-1 is IL-1α.

4. A method according to claim 3, wherein the IL-1 is human IL-1α.

5. A method according to claim 4, wherein the IL-1 is recombinant human IL-1α.

6. A method according to claim 5, wherein the colony stimulating factor is selected from the group consisting of GM-CSF, CSF-1, and G-CSF.

7. A method according to claim 2, wherein the IL-1 is IL-1β.

8. A method according to claim 7, wherein the IL-1 is human IL-1β.

9. A method according to claim 8, wherein the IL-1 is recombinant human IL-1β.

10. A method according to claim 9, wherein the colony stimulating factor is selected from the group consisting of GM-CSF, CSF-1, and G-CSF.

* * * * *